United States Patent
Lechner

(10) Patent No.: US 8,202,211 B2
(45) Date of Patent: Jun. 19, 2012

(54) CONTROLLABLE STOMACH BAND

(76) Inventor: Wolfgang Lechner, Judenau/Pixendorf (AT)

( * ) Notice: Subject to any disclaimer, the term of this patent is extended or adjusted under 35 U.S.C. 154(b) by 1275 days.

(21) Appl. No.: 11/886,751

(22) PCT Filed: Apr. 11, 2006

(86) PCT No.: PCT/AT2006/000145
§ 371 (c)(1),
(2), (4) Date: Sep. 20, 2007

(87) PCT Pub. No.: WO2006/108203
PCT Pub. Date: Oct. 19, 2006

(65) Prior Publication Data
US 2009/0054914 A1    Feb. 26, 2009

(30) Foreign Application Priority Data
Apr. 11, 2005    (AT) .................................. A 601/2005

(51) Int. Cl.
*A61F 2/00*    (2006.01)
(52) U.S. Cl. ........................................ 600/37
(58) Field of Classification Search .......... 600/37; 606/151, 157, 191, 192; 623/23.64, 23.67, 623/23.68; 607/40
See application file for complete search history.

(56) References Cited

U.S. PATENT DOCUMENTS

| 4,721,509 | A | 1/1988 | Craggs |
| 4,803,985 | A * | 2/1989 | Hill ................................ 606/157 |
| 6,475,136 | B1 | 11/2002 | Forsell |
| 7,502,649 | B2 | 3/2009 | Ben-Haim et al. |

FOREIGN PATENT DOCUMENTS

| EP | 0 876 808 | 11/1998 |
| WO | 2004/014245 | 2/2004 |
| WO | 2004/112563 A2 | 12/2004 |
| WO | 2005/009305 | 2/2005 |

OTHER PUBLICATIONS

English Translation of Japanese Office Action in Application No. 2008-504570 Dated Jul. 29, 2011.

* cited by examiner

*Primary Examiner* — Samuel Gilbert
(74) *Attorney, Agent, or Firm* — Ladas & Parry LLP

(57) ABSTRACT

The invention relates to a controllable stomach band (1) comprising a non-extendible rear (4) and a chamber (2) which is arranged on the stomach-side of the rear (4) and is used to control the restriction of the stomach by the supply or discharge of a liquid or a fluid into or out of the chamber (2). The aim of the invention is create one such stomach band (2), with which, during a corresponding rise in pressure in the stomach-restricting chamber (2), triggered for example by the passage of a swallowed bolus, the stomach can be temporarily enlarged to enable the bolus to pass easily and liquid to flow out via the stomach opening. To this end, a pressure chamber (6) is provided outside the rear (4), said pressure chamber being connected to the stomach-restricting chamber (2) by means of a pressure valve (5).

13 Claims, 3 Drawing Sheets

CONTROLLABLE STOMACH BAND

The invention relates to a controllable gastric band including a nonextensible back and a chamber arranged on the stoma side of the back for controlling the stoma restriction by supplying and discharging liquid, or fluid, respectively, to and from said chamber.

The invention relates to a further development of the controllable gastric band offered by several manufacturers in basically identical configurations (e.g., Swedish Band by Obtech (Johnson & Johnson), Lapband by Bioenterics, . . . ). This is a band used to limit food intake, which is wrapped around the uppermost stomach portion or esophagus and closed.

WO 01/24742 A1 describes a gastric band which is placed around the stomach like a belt and tightened. The adjustment of the stoma restriction is feasible in a purely mechanical manner by restricting the band.

U.S. Pat. No. 4,592,339 A describes a gastric band in which a chamber is arranged on the band side facing the stomach, which chamber can be filled with a liquid. A control of the stoma width is thereby enabled. The filling with liquid and emptying of the system may be realized through a subcutaneously sewn-in port, which is connected with the chamber of the gastric band via a flexible hose.

WO 03/020183 A1 discloses a gastric band that is surrounded by a viscoelastic material to protect the stomach.

Finally, WO 2005/009305 A1 discloses a gastric band which comprises a mechanically or electrically controlled and effected autoregulatory change of the stoma width aimed at overcoming the problems occurring with the presently used gastric bands and obtaining improved long-term results. For, it is true that presently used gastric bands in most cases yield good long-term results in terms of weight reduction and patient satisfaction, yet there are some problems which become particularly prominent with high band fillings. Many patients have, thus, reported on the unpleasant phenomenon of sialemesis, or regurgitation, respectively, primarily in the recumbent position. Food particles may remain in the esophagus above the stoma for quite some time, start fermenting there and hence provoke, in addition to bad breath, an irritation of the mucous membrane involving pain. A permanently high restriction of the stoma will over months lead to a decrease of the esophagial motility and in some cases to an increasing expansion of the esophagus, which will finally cause the esophagial sensitivity to fade away and the band effect to be lost, which will result in an increase in weight despite the highly filled gastric band applied.

WO 2005/009305 A1 tries to eliminate the problem faced with the presently used gastric bands in that the adjusted stoma width does not constantly remain the same, but will change in an auto-regulatory manner according to demand. What is sought is an increasing stoma restriction during eating, which disappears again upon termination of the food intake.

Departing from the prior art with the presently used gastric band, and as opposed to the just mentioned patent application WO 2005/009305 A1, the invention aims at providing a gastric band in which at a respective pressure increase in the chamber of the gastric band a temporary extension of the stoma and, hence, the passage of the bolus through the stoma is enabled. It is an object to provide a gastric band with a dynamic change of the stoma width.

The object according to the invention is achieved by a gastric band of the above-indicated type, in which a pressure chamber is provided on the exterior of the back, which pressure chamber is connected to the stoma-restricting chamber via a pressure valve. The gastric band is so narrowly adjusted in its stoma width as to be hardly passable by the swallowed food. The esophagial peristaltic conveys the bolus into the small stomach portion above the band. The narrow stoma constitutes a flow impediment for the bolus. As a result, a high intrabolus pressure is generated, which will finally reach the pressure of the peristaltic wave (40-80 mmHg). At a pressure increase, the pressure valve according to the invention is opened by the bolus, a portion of the liquid flows over from the stoma-restricting chamber of the gastric band into the pressure chamber, thus causing the extension of the stoma and enabling the passage of the bolus. The gastric band according to the invention causes a lag effect on the food passage in order to reach an early sense of fullness for the bearer of the band and, hence, reduce the food quantity taken in. With the presently available gastric bands, the adjusted stoma width usually remains unchanged.

Advantageously, the opening behaviour of the pressure valve is controllable. By an appropriate adjustment of the pressure valve, the behaviour of the gastric band can be changed and adapted to the patient's individual situation.

According to a further feature of the invention, the pressure valve is controllable with respect to the pressure level at which the pressure valve will open.

Control of the pressure valve may, e.g., be effected mechanically.

It is possible to effect the mechanical control of the pressure valve by aid of a liquid, or fluid, respectively.

Likewise, the mechanical control of the pressure valve may be effected via a second port chamber which is connected with the valve by a connecting hose.

Finally, the control of the pressure valve may also be effected electronically.

Advantageously, the pressure chamber is designed to be elastic so that, due to its elastic properties, it is capable of storing volume at an elevated pressure. Thus, when opening the pressure valve, the liquid, or fluid, respectively, flowing off into the pressure container will be intermediately stored in the pressure chamber under an elevated pressure.

In order to make it possible that, after passage of the bolus, an increased pressure will again be exerted on the stomach by the stoma-restricting chamber, the pressure chamber is connected to the stoma-restricting chamber via a backflow channel including a non-return valve. Thus, the liquid or fluid, respectively, temporarily stored in the pressure chamber will empty again into the stoma-restricting chamber of the gastric band via the backflow channel and the non-return valve immediately after the bolus has passed, the initial state thus being restored.

Advantageously, the pressure valve is connected to a means for a temporal control. In this way it is possible to influence the behaviour of the pressure valve as a function of time. During the night hours, the pressure valve may, e.g., be adjusted such that already at a slight pressure increase, the stoma-restricting chamber will become larger, thus enabling the passage of a bolus or the flowing off of saliva. On the other hand, the pressure at which the pressure valve will open can be adjusted to be higher in the morning hours, thereby making the intake of food in the morning more difficult.

If a means for detecting peristaltic waves is provided, which means is connected to the pressure valve, the behaviour of the pressure valve can also be influenced and controlled as a function of the food intake. For instance, at the beginning of the eating procedure, i.e., at the first passing peristaltic waves and, hence, pressure increases, the valve may be opened completely already at slight pressure increases of about 30 mmHg, which enables the bolus to pass without any problems. After some minutes, higher opening pressures will be required and/or only every second or third pressure increase will result in an opening of the pressure valve. The thus produced back-up of the bolus causes an increasing sense of fullness. Vomiting is prevented by causing the valve to open at high pressure increases, which causes the stoma to widen and enables the bolus to pass. Some minutes upon completion of the meal, the pressure valve will resume its original behaviour, thus opening already at slight pressure increases. The secondary peristaltic waves triggered if the bolus does not flow off completely can cause the food particles to flow off.

If on the stoma-side of the back, at least one auxiliary chamber is provided, an adaptation of the gastric band to the thickness of the gastric wall as well as to the amount of adipose and connective tissues additionally enclosed in the gastric band, which vary from one person to the other, can be effected. By filling the at least one auxiliary chamber, the basic pressure in the gastric band can be adjusted. With an increasing filling volume of the auxiliary chamber, also the pressure in the stoma-restricting chamber will increase. Advantageously, this at least one auxiliary chamber is not included in the liquid circulation between the stoma-restricting chamber and the pressure chamber.

For adjusting the basic pressure, the stoma-restricting chamber and/or the at least one auxiliary chamber advantageously are connected to a port to be arranged subcutaneously. By filling the port with liquid or a fluid, or sucking off liquid from the port, respectively, the basic pressure can be adjusted. Of course, also autonomously operating ports in which the liquid or the fluid, respectively, is shifted from a reservoir into the stoma-restricting chamber, or into the at least one auxiliary chamber, respectively, are possible.

According to a further embodiment of the invention, the pressure chamber is arranged in or adjacent to the port. This means that the pressure chamber which is connected to the stomarestricting chamber via the pressure valve, need not necessarily be arranged in the vicinity of the back of the gastric band, but may, e.g., also be located within or adjacent to the subcutaneously arranged port. If the pressure valve opens at the slightest pressure, the gastric band has the property to act in a pressure-stabilizing manner. The pressure increase in the stoma-restricting chamber is absorbed in the pressure chamber and thereby reduced. The characteristics and, thus, the properties of the gastric band will depend on the elastic properties of the pressure chamber.

The invention will be explained in more detail by way of the attached Figures. Therein:

Figure 1:
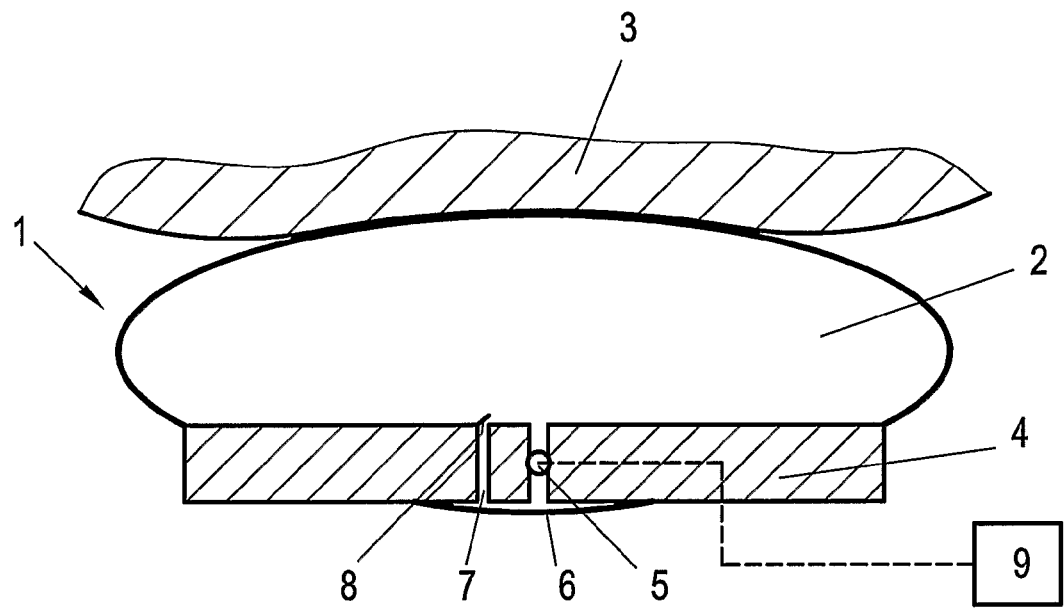
FIG. 1 shows a schematic cross section through an embodiment of a gastric band prior to the opening of the pressure valve.

FIG. 1 shows a cross section through a gastric band 1 comprising a liquid-filled chamber 2 and a non-extensible back 4. The liquid-filled chamber 2 lies at the gastric wall 3 so that the stomach can be restricted more or less as a function of the filling of the chamber 2. According to the invention, via a pressure valve 5, the stoma-restricting chamber 2 is connected to a pressure chamber 6 located externally of the back 4. Via a backflow channel 7 with a non-return valve 8, the liquid from the pressure chamber 6 can be returned to the stoma-restricting chamber 2. Instead of a liquid, theoretically, also a gas can be used as a filling for the chamber 2.

Figure 2:
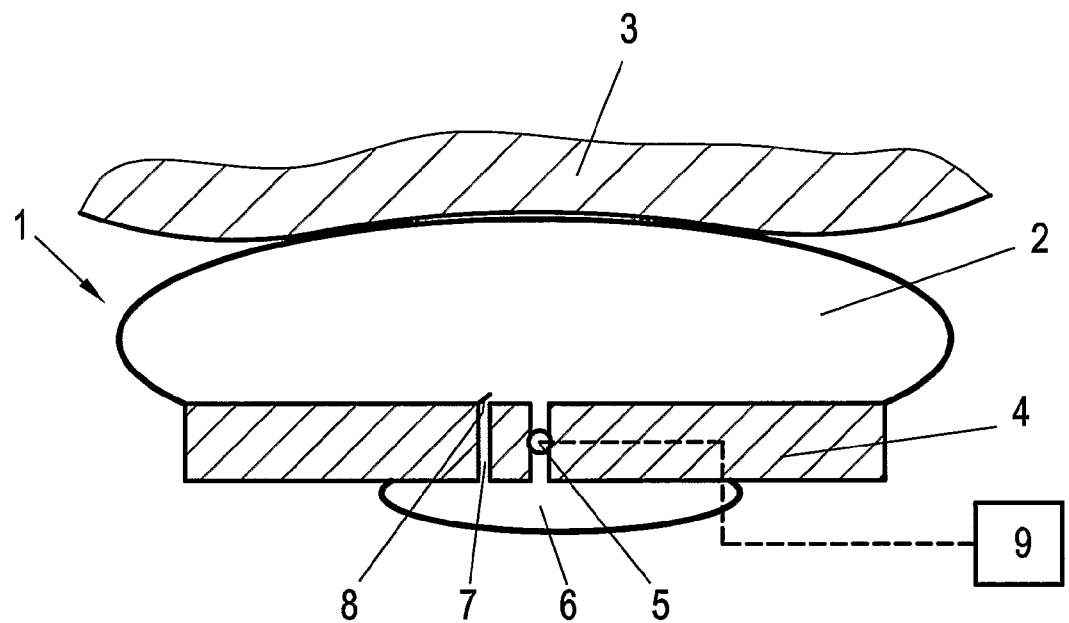
FIG. 2 shows a schematic cross section through the gastric band according to FIG. 1 after the transfer of liquid into the pressure chamber.

At a pressure increase in the chamber 2, the pressure valve opens and liquid from the chamber 2 flows over into the pressure chamber 6. The pressure chamber 6 can be designed to be elastic, thereby having the property of storing the pressed-in liquid at an elevated pressure. The stoma is thus widened, a bolus can pass more easily. This situation is illustrated in FIG. 2. After the passage of the bolus, the pressure in the chamber 2 will drop again such that the liquid temporarily stored in the pressure chamber 6 at an elevated pressure will again be able to flow back into the chamber 2 via the backflow channel 7 including the non-return valve 8.

The opening behaviour of the pressure valve preferably is designed to be controllable, wherein this control can be mechanically or electronically effected. Furthermore, the pressure valve 5 can be connected to a means 9 for a temporal control, such as indicated in FIGS. 1 and 2. Thereby, the pressure valve 5 can be controlled as a function of the time of the day. The pressure at which the pressure valve 5 will open may, e.g., be adjusted to be higher during the morning hours, making an intake of food in the morning hours more difficult. Likewise, the pressure at which the pressure valve 5 will open can be reduced during the night hours in order that saliva or food particles accumulated above of the stoma can pass the stoma and be conducted away.

Figure 3:
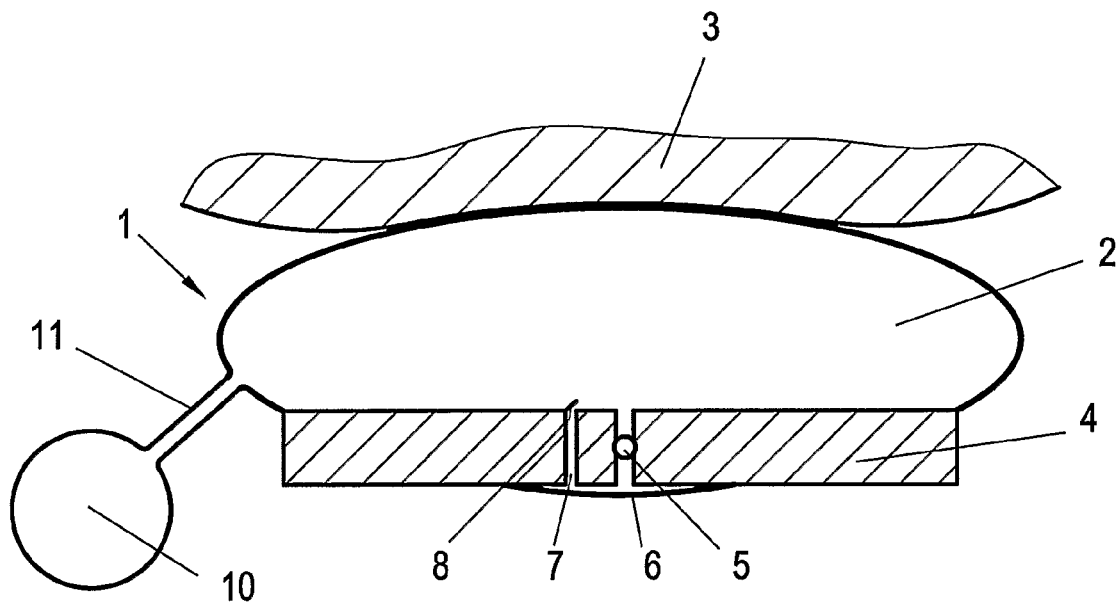
FIG. 3 shows a further embodiment of a gastric band with a subcutaneously arranged port.

FIG. 3 shows a variant of the gastric band 1 according to the invention, wherein the stoma-restricting chamber 2 is connected via a corresponding duct 11 to a port 10 to be arranged subcutaneously. By supplying and draining liquid via the port 10 to and from stoma-restricting chamber 2, an adaptation of the gastric band 1 to the respective conditions can be effected.

Figure 4:
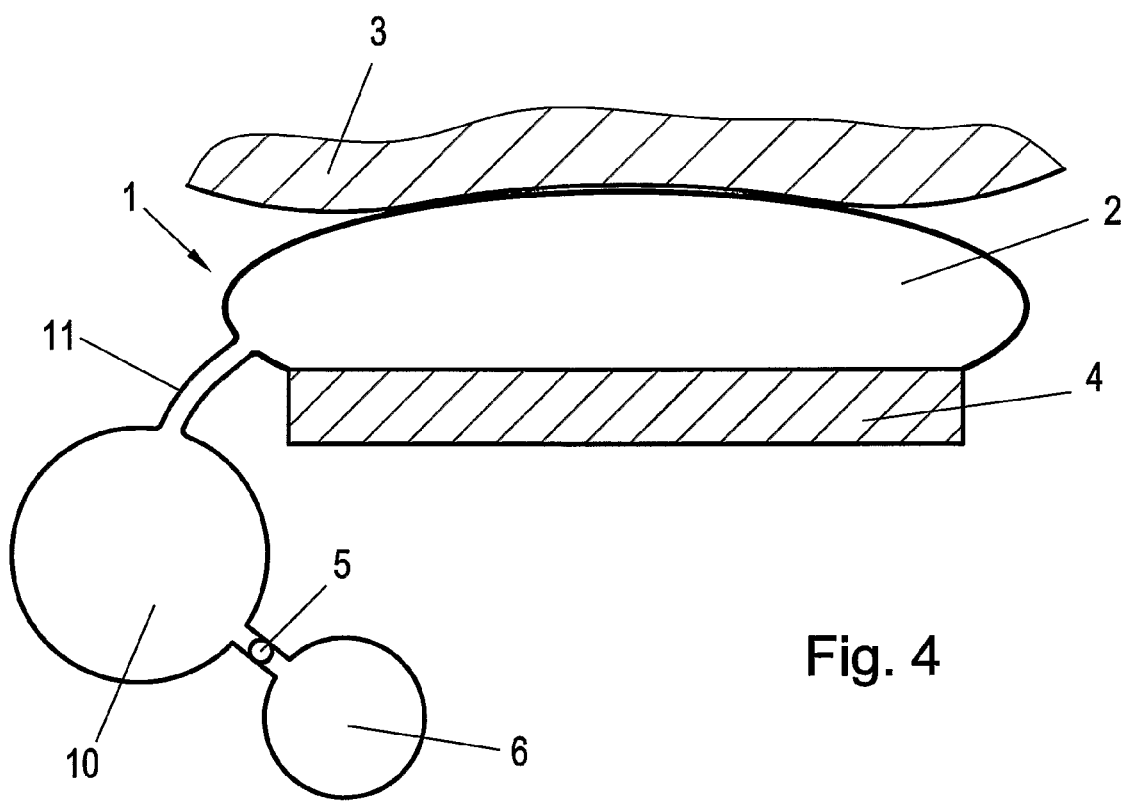
FIG. 4 shows a further embodiment of a gastric band with a subcutaneous port and a pressure chamber arranged next to it.

In the embodiment variant of a gastric band 1 according to FIG. 4, the pressure chamber 6 is not arranged immediately behind the back 4, but next to the port 10. During a pressure increase in the stoma-restricting chamber 2, the former is transmitted via the duct 11 into the port 10, where the pressure valve 5 will open when a respective pressure has been reached and the liquid will be conveyed into the pressure chamber 6. When the pressure in the stoma-restricting chamber 2 is reduced, the liquid will again be conveyed from the pressure chamber 6 into the port 10. This may, e.g., be achieved by a special pressure valve 5 which operates in both directions, or via a return channel as has been illustrated in the embodiments according to FIGS. 1 to 3.

Figure 5:
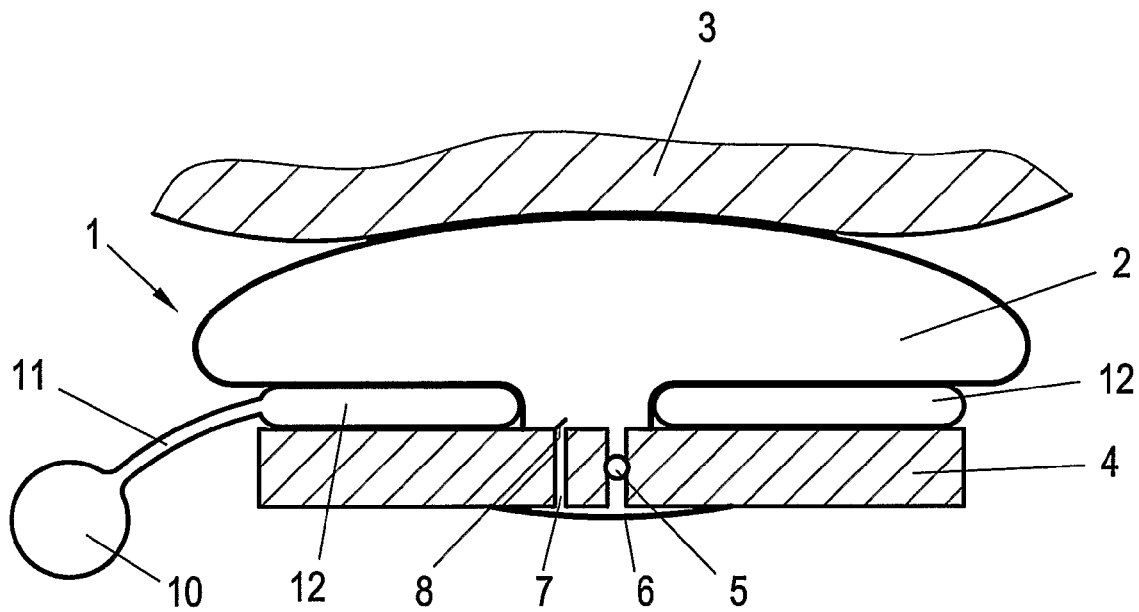
FIG. 5 shows a further embodiment of a gastric band with at least one auxiliary chamber.

The embodiment of a gastric band 1 according to FIG. 5 differs from the variant according to FIG. 1 in that at least one auxiliary chamber 12 is, e.g., annularly, arranged below the stoma-restricting chamber 2, which auxiliary chamber 12 is connected via a duct 11 to a port 10 to be arranged subcutaneously. Via this auxiliary chamber 12, the basic adjustment of the pressure of the gastric band 1 can be effected. In this connection, the auxiliary chambers 12 are not included in the liquid circulation between the stoma-restricting chamber 2 and the pressure chamber 6. By supplying and draining liquid to and from the port 10, respectively, an adaptation of the gastric band 1 to the individually different layer thicknesses of the gastric wall 3 and adipose tissue enclosed by the gastric band 1 can be achieved.

Figure 6:
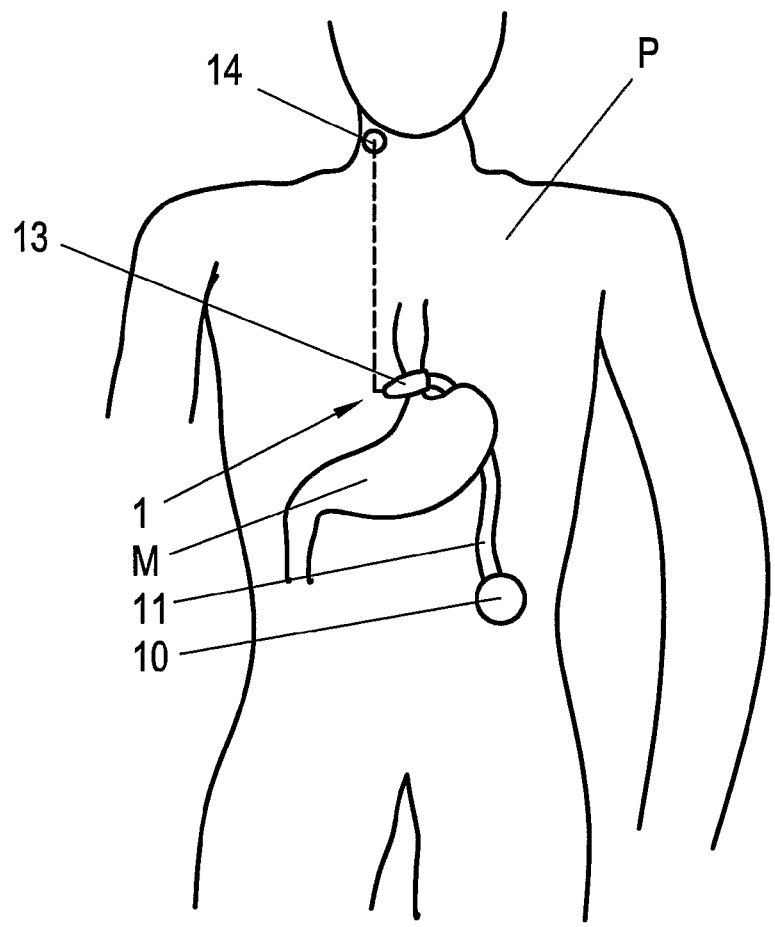
FIG. 6 shows a schematic illustration of an implanted gastric band with a subcutaneously arranged port and sensors for detecting peristaltic waves as well as the swallowing activity of the patient.

FIG. 6 schematically shows an application of the gastric band 1 according to the invention which encloses the entrance of the stomach M of the patient P. Via a duct 11, the stoma-restricting chamber 2 (not illustrated) of the gastric band 1 is connected to a port 10 to be arranged subcutaneously, via which the basic pressure which the gastric band 1 will exert on the gastric wall can be adjusted. The pressure valve 5 of the gastric band 1 may, e.g., be connected to a device 13 for detecting peristaltic waves so that a control of the pressure valve 5 as a function of the peristaltic waves or of the intake of food, respectively, will become possible. Likewise, the pressure valve 5 can also be connected to a sensor 14 for measuring the swallowing activity. The connection between the sensor 14 for measuring the swallowing activity and the pressure valve 5, or a respective electronic system (not illustrated) may, e.g., be effected by radio communication.

The invention claimed is:

1. A controllable gastric band (1) including a nonextensible back (4) and a stoma-restricting chamber (2) disposed on a stoma side of the back (4) for controlling stoma restriction by supplying and discharging a liquid or other fluid to and from said stoma-restricting chamber (2), a pressure chamber (6) disposed on or below an exterior side of the back (4), which pressure chamber is connected to the stoma-restricting chamber (2) via a pressure valve (5) that opens when a threshold pressure in the stoma-restricting chamber is reached to allow liquid or fluid from the stoma-restricting chamber to flow into the pressure chamber, wherein the pressure valve (5) is adjustable such that the threshold pressure at which the pressure valve opens to allow liquid or fluid from the stoma-restricting chamber to flow into the pressure chamber can be raised or lowered by adjustment of the pressure valve.

2. A gastric band (1) according to claim 1, comprising means for controlling the threshold pressure at which the pressure valve (5) will open.

3. A gastric band (1) according to claim 1, comprising means for adjusting the pressure valve (5) mechanically.

4. A gastric band (1) according to claim 3, wherein the means for mechanical adjustment of the pressure valve comprises a liquid or a fluid.

5. A gastric (1) according to claim 1, comprising means for control of the pressure valve (5) electronically.

6. A gastric band (1) according to claim 1, wherein the pressure chamber (6) is elastic so that, due to its elastic properties, it is capable of storing volume at an elevated pressure.

7. A gastric band (1) according to claim 1, wherein the pressure chamber (6) is connected to the stoma-restricting chamber (2) via a backflow channel (7) including a non-return valve (8) so that the liquid stored in the pressure chamber (6) at an elevated pressure can be conveyed back into the stoma-restricting chamber (2).

8. A gastric band (1) according to claim 1, comprising means for temporal control of the pressure valve (5) to permit the threshold pressure at which the pressure valve opens to be controlled as a function of the time of day.

9. The gastric band (1) according to claim 1, comprising means (13) connected to the pressure valve 5 for detecting peristaltic waves.

10. A gastric band (1) according to claim 1, comprising on the stoma-side of the back (4), at least one auxiliary chamber (12).

11. A gastric band (1) according to claim 10, wherein the stoma-restricting chamber (2) or the at least one auxiliary chamber (12) is connected to a port (10).

12. A gastric band (1) according to claim 11, wherein the pressure chamber (6) is adjacent to the port (10).

13. A gastric band (1) according to claim 1, comprising a sensor (14) for measuring swallowing activity, wherein the sensor is connected to the pressure valve (5).

* * * * *